United States Patent [19]
Cherkez et al.

[11] Patent Number: 5,414,129
[45] Date of Patent: May 9, 1995

[54] PROCESS FOR THE PURIFICATION OF 2-[(DIMETHYLAMINO)METHYL]-1-(3-METHOXYPHENYL)CYCLOHEXANOL AND ITS SALTS

[75] Inventors: Stephen Cherkez; Ori Lerman, both of Ramat Gan; Michael Tennenbaum, Kiryat Ono; Hasalia Avner, Ashdod; Tamar Kunyevski, Rehovot, all of Israel

[73] Assignee: Chemagis, Ltd., Bnei Brak, Israel

[21] Appl. No.: 117,803

[22] Filed: Sep. 8, 1993

[30] Foreign Application Priority Data

Sep. 8, 1992 [IL] Israel ..................... 103096

[51] Int. Cl.$^6$ .................. C07C 209/84; C07C 209/86; C07C 209/88
[52] U.S. Cl. ..................... 564/425; 564/438; 564/443
[58] Field of Search ............. 564/304, 425, 438, 443

[56] References Cited
U.S. PATENT DOCUMENTS

| | | | |
|---|---|---|---|
| 3,452,011 | 6/1969 | Skaletzky | 540/484 |
| 3,652,589 | 3/1972 | Flick et al. | 564/304 |
| 3,830,934 | 8/1974 | Flick et al. | 514/646 |

OTHER PUBLICATIONS

Flick et al., Arzneim–Forsch., 28(1A), 107–13 (1978).
Frankus et al., Arzneim.–Forsch., 28(1A, 114–21 (1978).
Eiden et al., Arch. Pharm., vol. 320(11), pp.1099–1103 (1987).
Shirai et al., Nagoya Shiritsu Daigaku Kenkyu Nempo, vol. 21, pp. 18–21 (1973).
Yashiro et al., Chem. Pharm. Bull, vol. 23(9), pp. 2054–2057 (1975).

*Primary Examiner*—Glennon H. Hollrah
*Assistant Examiner*—Scott C. Rand
*Attorney, Agent, or Firm*—Popham, Haik, Schnobrich & Kaufman, Ltd.

[57] ABSTRACT

A process for the improved purification and separation of trans 2-[(dimethylamino)methyl]-1-(3-methoxyphenyl)cyclohexanol hydrochloride from a reaction mixture containing the trans isomer, the cis isomer and Grignard reaction side products, comprising combining the mixture with a solution of hydrochloric acid in a low molecular weight alcohol or with gaseous hydrogen chloride in the presence of an organic solvent selected from medium molecular weight alcohols, ketones, esters and ethers or aromatic ethers, to effect the selective precipitation of trans 2-[(dimethylamino)methyl]-1-(3-methoxyphenyl)cyclohexanol hydrochloride.

6 Claims, No Drawings

PROCESS FOR THE PURIFICATION OF 2-[(DIMETHYLAMINO)METHYL]-1-(3-METHOXYPHENYL)CYCLOHEXANOL AND ITS SALTS

The present invention relates to a process for the purification of 2-[(dimethylamino)methyl]-1-(3-methoxyphenyl)cyclohexanol and its salts.

More particularly the present invention relates to a process for the improved purification and separation of trans 2-[(dimethylamino)methyl]-1-(3-methoxyphenyl)-cyclohexanol (also known as Tramadol), from its cis-isomer and undesirable side-products by selective precipitation of its hydrochloride in non-toxic media.

Tramadol is a long-established drug invented by Gruenenthal GmbH Germany, which is used as a non-addicting analgesic and sold under tradenames such as Tramal or Crispin.

The synthesis of Tramadol is described in U.S. Pat. No. 3.652.589 and in British Pat. No. 992.399.

The structure of Tramadol is described in formula i (trans-isomer) which is obtained as the major synthetic product. The cis isomer is described by formula ii and is obtained as a minor component of the reaction mixture.

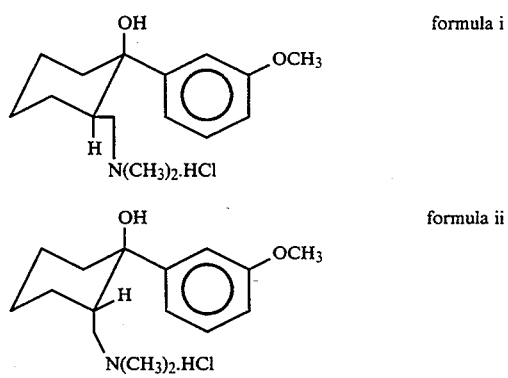

The original patents describe the isolation of the pure trans Tramadol from the isomer mixture as follows: the complex mixture obtained from the Grignard reaction is distilled in high vacuum. Both geometrical isomers of Tramadol boil around 138° C.–140° C. (0.6 mm Hg). The distilled isomer mixture is dissolved in diethyl ether and treated with gaseous hydrogen chloride; and the crude mixture of cis and trans Tramadol hydrochloride is precipitated and filtered. This procedure yields an isomer mixture with a relatively high content of cis-isomer.

The isomer mixture is then refluxed with five-fold volume of moist dioxane, and the resulting suspension is filtered while still hot. The cake is boiled once more with dry dioxane and filtered; the residue obtained consists of pure trans Tramadol hydrochloride.

Dioxane is a solvent with many undesirable properties. It has recently been listed as category I carcinogen by OSHA. (Kirk & Othmer, 3rd edition vol. 9, page 386), and as causing CNS depression and necrosis of liver and kidneys. (ibid, vol. 13, page 267).

In addition, dioxane poses safety threats by forming hazardous peroxides (Kird & Othmer, 3rd edition, vol. 17, page 48).

Dioxane as a solvent residue in drugs has recently been subjected to scrutiny as a possible toxic component, and the limit set for its content is extremely low: in the order of several ppb's.

Alternative solvents effectively separating the isomers are very hard to find.

After experimenting with various solvents and solvent mixtures and separation conditions, it has surprisingly been found that a very effective isomer separation is performed by treating a mixture of isomers in an organic solvent solution with hydrochloric acid and carefully monitoring the selective precipitation of the isomer hydrochlorides. In addition, the process described in this invention, does not necessarily require a high vacuum distillation of the isomers prior to their isolation.

Thus according to the present invention there is now provided a process for the improved purification and separation of trans 2-[(dimethylamino)methyl]-1-(3-methoxyphenyl)cyclohexanol hydrochloride from a reaction mixture containing the trans-isomer, its cis isomer and Grignard reaction side products comprising treating said mixture with a solution of hydrochloric acid in a low molecular weight alcohol or with gaseous hydrogen chloride in the presence of an organic solvent selected from medium molecular weight alcohols, ketones, esters and ethers or aromatic ethers to effect the selective precipitation of trans 2-[(dimethylamino)methyl]-1-(3-methoxyphenyl)cyclohexanol hydrochloride.

In preferred embodiments of the present invention said organic solvent is selected from a $C_3$–$C_8$ polyhydric alcohol, a $C_3$–$C_8$ ketone, a $C_{12}$–$C_7$ ester or mixture thereof.

Preferably, alcohols are used as they are not reactive in the precipitation conditions.

Alcohols such as $C_4$ to $C_7$ alcohols are the most effective, with $C_5$ and $C_6$ isomers alcohols as the preferred embodiment of this patent.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

The following examples more fully illustrate the present invention:

EXAMPLE A

The crude base was prepared via the Grignard reaction as follows:

0.1 mole of magnesium turnings is mixed with 10 ml of dry THF. A solution of 0.1 ml. 3-bromoanisole in 50 ml. THF is added dropwise, at such a rate that a mild reflux is maintained. The reaction mixture is cooled in an ice bath and a solution of 0.1 ml of 2-dimethylamino methyl cyclohexanone in 20 ml THF is added dropwise during a 3 hour period.

The reaction is quenched in 100 ml of saturated ammonium chloride solution. The organic solution is separated and evaporated. The crude basic solution can be used as such for isomer separation.

EXAMPLE 1

175 gr. of the crude mixture obtained from the Grignard reaction between 3-methoxyphenyl magnesium bromide and 2-dimethylamino-methylcyclohexanone (containing roughly 60% of trans Tramadol—base and 10% of the cis isomer), produced essentially as described in a paper (R. Flick, E. Frankus and E. Friederichs, Arzneim. Forsch. 28, 107 (1978) (see example A), is dissolved in 350 ml. of 2-propanol.

100 ml. of isopropanolic HCl (25% w/w) is introduced thereinto during one hour. The mixture is stirred and cooled to 20° for an additional 3 hour period. The precipitate formed consisting mainly of the trans isomer is filtered and recrystallized twice from isopropanol. A mixture containing 97.8% of the trans tramadol and 2.2% of the cis isomer is obtained.

EXAMPLES 2-11

The procedure described in Example 1 was repeated, replacing the 2-propanol with the solvents described in Table 1.

TABLE I

| EXAMPLE | SOLVENT | % TRANS | % CIS | YIELD (%) TRANS |
|---|---|---|---|---|
| 2 | BUTYL ACETATE | 89.5 | 10.5 | 61.0 |
| 3 | MIBK | 86.6 | 13.3 | 65.6 |
| 4 | 1-BUTANOL | 98.1 | 1.9 | 50.0 |
| 5 | 1-PENTANOL | 98.3 | 1.7 | 58.2 |
| 6 | PAA * | 98.2 | 1.8 | 60.0 |
| 7 | 1-HEXANOL | 98.0 | 2.0 | 65.8 |
| 8 | CYCLOHEXANOL | 99.0 | 1.0 | 42.0 |
| 9 | 1-OCTANOL | 98.1 | 1.9 | 45.0 |
| 10 | 2-ETHYL HEXANOL | 97.3 | 2.7 | 38.0 |
| 11 | ANISOLE | 89.2 | 10.2 | 62.4 |

* Primary amyl alcohols mixture.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for the improved purification and separation of trans 2-[(dimethylamino)methyl]-1-(3-methoxyphenyl)cyclohexanol-hydrochloride from a reaction mixture containing the trans-isomer, the cis-isomer and Grignard reaction side products comprising combing said mixture with a solution of hydrochloric acid in a $C_2$-$C_3$ alcohol or with gaseous hydrogen chloride in the presence of an organic solvent selected from among the group consisting of $C_3$-$C_8$ alcohols, $C_3$-$C_8$ ketones, $C_2$-$C_7$ esters, and anisole to effect the selective precipitation of trans 2-[(dimethylamino)methyl]-1-(3 methoxyphenyl) cyclohexanol-hydrochloride.

2. A process according to claim 1 wherein said organic solvent is selected from a $C_3$-$C_8$ polyhydric alcohol, a $C_3$-$C_8$ ketone, a $C_2$-$C_4$ ester or a mixture thereof.

3. A process according to claim 1 in which the medium molecular weight alcohols are pentanols or hexanols.

4. A process according to claim 1 by which the selective purification is effected on the crude reaction mixture without distillation.

5. A process according to claim 1 in which the hydrochloric acid is introduced as a solution.

6. A process according to claim 5 wherein said hydrochloric acid is introduced as a solution in isopropanol as said lower alcohol.

* * * * *